(12) United States Patent
Beilfuss et al.

(10) Patent No.: US 8,093,193 B2
(45) Date of Patent: Jan. 10, 2012

(54) COMPOSITION BASED ON GLYCEROL ETHER/POLYOL MIXTURES

(75) Inventors: Wolfgang Beilfuss, Hamburg (DE); Sabine Wutsch, Hamburg (DE); Klaus Weber, Hamburg (DE); Ralf Gradtke, Tornesch (DE)

(73) Assignee: Air Liquide Sante (International), Paris (FR)

( * ) Notice: Subject to any disclaimer, the term of this patent is extended or adjusted under 35 U.S.C. 154(b) by 0 days.

(21) Appl. No.: 13/112,340

(22) Filed: May 20, 2011

(65) Prior Publication Data

US 2011/0218250 A1 Sep. 8, 2011

Related U.S. Application Data

(62) Division of application No. 12/101,171, filed on Apr. 11, 2008, now Pat. No. 8,058,218.

(30) Foreign Application Priority Data

Apr. 16, 2007 (DE) .......................... 10 2007 017 851

(51) Int. Cl.
*C11D 3/20* (2006.01)
*C11D 9/26* (2006.01)
*A61K 8/34* (2006.01)

(52) U.S. Cl. ........ 510/130; 510/119; 510/437; 510/506; 510/525; 424/401

(58) Field of Classification Search .................. 510/119, 510/130, 437, 506, 525; 424/401
See application file for complete search history.

(56) References Cited

U.S. PATENT DOCUMENTS

| 6,040,347 | A | 3/2000 | Cupferman |
| 2002/0098211 | A1 | 7/2002 | Cupferman |
| 2003/0152644 | A1 | 8/2003 | Modak |
| 2004/0208782 | A1 | 10/2004 | Beilfuess |
| 2006/0165612 | A1 | 7/2006 | Beilfuess |
| 2008/0050331 | A1 * | 2/2008 | Giacomoni et al. ........ 424/70.14 |

FOREIGN PATENT DOCUMENTS

| DE | 4026756 | | 2/1992 |
| DE | 4140474 | | 6/1993 |
| DE | 100 25 124 | A1 | 11/2001 |
| DE | 10028207 | | 1/2002 |
| DE | 2004043336 | | 2/2004 |
| DE | 10 2005 029 776 | A1 | 11/2006 |
| EP | 1683417 | | 7/2006 |
| JP | 2003-213174 | A | 8/2005 |
| JP | 2005213174 | * | 8/2005 |
| WO | 98/22081 | A | 5/1998 |
| WO | 03/084553 | A1 | 10/2003 |
| WO | 20080067182 | | 1/2008 |
| WO | WO 2008/006718 | * | 1/2008 |

OTHER PUBLICATIONS

Anonymous: "Botanigenics launches paraben-free preservative system" Cosmetics and Toiletries, Feb. 7, 2006.

* cited by examiner

*Primary Examiner* — Brian P Mruk
(74) *Attorney, Agent, or Firm* — Young & Thompson

(57) ABSTRACT

The invention relates to compositions which comprise one or more glycerol ethers together with one or more diol/diols and/or polyol/polyols. As a result, as well as good microbicidal effectiveness, whitening is reduced or avoided, drying-out of the skin is prevented, the moisture content is regulated and the skin is regreased to an adequate extent.

3 Claims, No Drawings

COMPOSITION BASED ON GLYCEROL ETHER/POLYOL MIXTURES

CROSS REFERENCE TO RELATED APPLICATIONS

This application is a division of application Ser. No.: 12/101,171 filed on Apr. 11, 2008, now U.S. Pat. No. 8,058,218; which claimed priority to German application 10 2007 017 851.6 filed Apr. 16, 2007. The entire contents of each of the above-identified applications are hereby incorporated by reference.

BACKGROUND OF THE INVENTION

The invention relates to compositions which, besides one or more glycerol ethers, comprise one or more polyols.

Alcohols, polyols and also glycerol ethers in general are used widely in the field of cosmetic, pharmaceutical, dermatological and also technical products. Criteria here are often antimicrobial effectiveness, and material and skin compatibility.

There is a constant need for compositions with improved properties, with applications to the skin and the feel which arises following application of the corresponding product, and the resulting appearance also increasingly playing a greater role. Often, following use of corresponding products, an unpleasant feeling of dryness, a feeling of stickiness and/or even an undesired visible residue presents itself, depending on the composition.

At a time of increasing hygiene awareness on the part of the consumer and increased use of cosmetic cleansing and care products, such as, for example, soaps, creams, deodorant products, shower and bath preparations, the increased use of alcohol-, soap- and surfactant-containing products on the skin also often results in the above-stated unpleasant accompanying phenomena.

The object of the invention is therefore to provide compositions with microbicidal and/or preservative and/or cosmetic effect and/or dermatological effect and/or pharmaceutical effect which do not exhibit, or exhibit to a reduced degree, the above-stated disadvantages and unpleasant accompanying phenomena. In this connection, while achieving a good or improved microbicidal and simultaneously regreasing effect it is necessary to prevent or restrict so-called "whitening".

This object is achieved through compositions which comprise one or more glycerol ethers together with one or more diols and/or polyols.

Preferred embodiments of the invention are subject matter of the dependent claims.

The invention also covers the use of such compositions in suitable products for achieving the effects desired in each case.

The glycerol ethers which can be used according to the invention are preferably mono-, di- or trialkyl, -aralkyl, -alkylaryl or -aryl glycerol ethers having, if present, in each case (also independently of one another) saturated or unsaturated, branched or unbranched $C_1$-$C_{24}$-alkyl groups, and, if present, $C_6$-$C_{10}$-aryl groups.

The glycerol ethers according to the invention have the formula

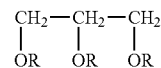

and are preferably glycerol monoalkyl ethers with the formula

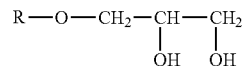

In the above formulae, R, in each case independently of the others, is preferably a straight- or branched-chain, saturated or unsaturated alkyl, aralkyl or alkylaryl group having preferably 6 to 18, in particular 7 to 12 and preferably 8 to 12, particularly preferably 8, carbon atoms in the alkyl group. These include, for example, the preferred 1-octadecyl glycerol ethers (also known as batyl alcohol), 1-hexadecyl glycerol ether (also known as chimyl alcohol), 1-(9-octadecenyl) glycerol ether (also known as selachyl alcohol), 1-dodecyl glycerol ether, 1-decyl glycerol ether, 1-(2-propylheptyl) glycerol ether, 1-octyl glycerol ether and 1-(2-ethylhexyl) glycerol ether (also referred to as 3-((2-ethylhexyl)oxy)-1,2-propanediol, where 1-(2-ethylhexyl) glycerol ether is particularly preferred.

It is also possible to use mixtures of glycerol ethers according to the invention.

The glycerol ethers used according to the invention, in particular the glycerol monoalkyl ethers, are colour- and odour-neutral compounds which can be produced in chemically pure form.

Derivatives with an alkyl radical having up to 9 carbon atoms which are liquid at room temperature can be incorporated into products particularly easily and are therefore preferred.

Of particular advantage is the greater chemical stability of the glycerol monoalkyl ethers compared to fatty acid esters, e.g. mono- and diglycerides. On account of their ether structure, they can also be used in the alkaline sector. This is particularly advantageous for use in liquid soaps where, at high pH values and a large water content, hydrolysis of the glycerides results with release of fatty acids, which manifests itself, inter alia, in a poor low-temperature stability of the corresponding products. Enzymatic cleavage with release of fatty acids, which can arise in the case of the glycerides, is also not to be feared in the case of the glycerol ethers.

The diols used according to the invention include alkanediols having 4 to 16 carbon atoms, preferably 6 to 10 carbon atoms, preferably 6 to 8 carbon atoms, in the alkylene chain, such as butylene glycols, pentanediols, hexanediols, heptanediols, octanediols and decanediols, in particular 1,2-butanediol, 1,2-pentanediol, 1,2-hexanediol, 1,2-heptanediol, 1,2-octanediol, and mixtures thereof, such as, for example, a mixture of 1,2-hexanediol and 1,2-octanediol.

The mixing ratio in mixtures of diols is arbitrary here and can be, for example, 10:1 to 1:10, preferably 5:1 to 1:5, in particular 2:1 to 1:2, particularly preferably 1:1.

Polyols used according to the invention include triols, such as glycerol and sugar alcohols, such as threitol, glucitol, sorbitol and inositol, or mixtures thereof.

Particular preference is given to the diols 1,2-hexanediol, 1,2-octanediol, a mixture of the same and the polyol glycerol.

The mixing ratio in mixtures of polyols is here again arbitrary and can be, for example, 20:1 to 1:20, preferably 10:1 to 1:10, more preferably 5:1 to 1:5 and in particular 2:1 to 1:2.

The compositions according to the invention comprise at least one glycerol ether in an amount of from 0.01 to 30 or 40% by weight, preferably 0.05 to 10% by weight, in particular 0.1 to 5% by weight, preferably 0.5 to 2 or 3% by weight.

In addition, they comprise at least one diol or polyol in an amount of from 0.01 to 99.99% by weight, preferably 0.05 to 40% by weight, in particular 0.1 to 10% by weight, preferably 0.5 to 5 or 8% by weight.

The use concentration of the components also varies as a function of the type and concentration of the other constituents, such as the washing-active substances and the further additives, and also depending on the strength of the desired effect, in particular the microbicidal, anti-whitening and regreasing effects.

Excluded from the present invention are aftershave formulations which comprise 1-(2-ethylhexyl) glycerol ether, glycerol and ethanol, and also day creams which comprise 1-dodecyl glycerol ether and glycerol.

Preferred compositions according to the invention comprise:
 glycerol monoalkyl ethers, in particular 1-(2-ethylhexyl) glycerol ether, together with 1,2-hexanediol, 1,2-octanediol, a mixture of 1,2-hexanediol and 1,2-octanediol, or
 glycerol monoalkyl ethers, in particular 1-(2-ethylhexyl) glycerol ether, together with glycerol.

The compositions according to the invention are antimicrobially or microbicidally effective and can be used in cosmetic, pharmaceutical, dermatological and also technical products (such as, for example, cooling lubricants) for deactivating microorganisms such as bacteria, yeasts, fungi and viruses, including microorganisms which are comparatively difficult to deactivate, such as mycobacteria, Mallasezia furfur, Propionibacterium acnes, and odour-causing microbes.

In particular, application to the skin is possible here without problems, something which is also due to the excellent regreasing properties, the imparting of a very pleasant feel on the skin and also a very good spreadability on the skin.

When applying cosmetic O/W emulsions (e.g. creams, lotions) to the skin, a troublesome effect is often observed, which is referred to as whitening effect. When using the compositions according to the invention, the troublesome "whitening" is advantageously avoided or considerably reduced.

Besides the glycerol ether(s) and diol(s) and/or polyol(s), the compositions according to the invention can also comprise suitable and optional additives, although these are not required for the preparation of the compositions according to the invention and can therefore also be omitted according to the most general embodiment of the invention.

Suitable additives are, for example, aliphatic alcohols, such as ethanol, isopropanol, n-propanol and fatty alcohols, aromatic alcohols, such as benzyl alcohol, phenethyl alcohol, phenylpropanols, phenoxyethanol, phenoxypropanols, and propylene glycol monobutyl ether, butyl diglycol, fatty alcohol esters and fatty acid esters. However, nonionic and ionic surfactants, glucosides and other customary auxiliaries, such as thickeners, emulsifiers, preservatives, dispersion auxiliaries etc. can also be used. Phenoxyethanol is a preferred additive here. Further functional additives are, for example, complexing agents and solubility promoters, which can be used particularly in the preparation of concentrates.

The compositions are preferably aqueous, aqueous/alcoholic or alcoholic. They can also be present in the form of a concentrate, a low-viscosity thin-liquid or higher-viscosity but flowable composition, a cream, salve or paste, or an emulsion (W/O or O/W).

The application temperature can range from ambient temperature or room temperature (20° C.) to, for example, 30° C., 37° C. or 50° C. or more, e.g. when used in masks.

The other additives of the composition are selected depending on the desired consistency or the desired field of use.

The compositions according to the invention can be in the form of an aqueous and/or alcoholic solution, cream or emulsion in which, in particular, a mixture with surface-active substances, in particular emulsifiers or surfactants, and/or other additives is present.

The compositions according to the invention can be used in particular in skincare products from the cosmetic and near-cosmetic sector. These include, for example, cleaning and care products, such as solid or liquid soaps, shower baths, shower gels, foam baths, shampoos, washing lotions, day creams, moisturizing creams, O/W or W/O care creams, O/W or W/O care emulsions, aftershave solutions or emulsions and hand dishwashing compositions.

The regreasing of the skin and the imparting of a pleasant feel on the skin and feeling of smoothness and the avoidance of stickiness following use also takes place surprisingly well through the combination of the glycerol ethers and di- and/or polyols present according to the invention. A silky, velvety, soft feel is produced in contrast to a waxy or oily feel. The spreadability and the ability to absorb on or in the skin is also improved.

To improve the stability, the organoleptic properties and to prevent or reduce the formation of undesired degradation products, it is particularly preferred to add stabilizers and/or antioxidants to the compositions according to the invention.

Examples of stabilizers and/or antioxidants are
 low-temperature stabilizers, such as lower alcohols, e.g. ethanol, propanols, glycols, e.g. 1,2-propylene glycol, glycol ethers,
 phenol compounds, such as 3-tert-butyl-4-hydroxyanisole, 2,6-di-tert-butyl-p-cresol, dodecyl gallate, pyrogallate, tocopherol (e.g. vitamin E), and its derivatives (e.g. vitamin E acetate), preferably vitamin E and its derivative, particularly preferably vitamin E.

The stabilizers and/or antioxidants can be present in the compositions in a concentration of from 0.0001% by weight to 5% by weight, preferably 0.001% by weight to 0.5% by weight, particularly preferably 0.01% by weight to 0.1% by weight, e.g. 0.015% by weight.

In addition, a good deodorizing effect and an increase in the preservative effect of other preservatives arises.

The compositions according to the invention can be used as concentrate or dilute use solutions. Suitable glycerol ether concentrations for concentrates are, for example, 10 to 40% by weight, in particular 15 to 30% by weight. Suitable glycerol ether concentrations for dilute use solutions are, for example, 0.1 to 5% by weight, preferably 1 to 3.0% by weight, or preferably 0.5 to 2.0% by weight.

The invention is further illustrated below by examples.

EXAMPLES

Example 1

Cream—Sensory Effect

An exemplary product according to the invention is a cream B with the following composition:

|  | % by wt. |
| --- | --- |
| Arachidyl alcohol/behenyl alcohol/arachidyl glucoside (standard commercial mixture Montanov ® 202) | 5 |
| Cetearyl octanoate (Lanol ® 1688) | 20 |
| 1-(2-Ethylhexyl) glycerol ether (Sensiva ® SC 50) | 1 |
| Polyacrylate-13/polyisobutene/polysorbate 20 (standard commercial mixture Sepiplus ® 400) | 0.2 |
| Water (demineralized) | 64.3 |
| Glycerol (85% strength) (corresponds to 8% by weight of glycerol as ingredient) | 9.4 |
| Benzyl alcohol/methylchloroisothiazolinone/methylisothiazolinone (standard commercial mixture Euxyl ® K 100) | 0.1 |
|  | 100 |

The comparison product used was a cream A with the same composition but in which the 1% by weight of glycerol ether had been replaced by 1% by weight of water.

The two creams A and B are assessed here by a group of subjects which have applied the particular product to the skin. The creams were each applied once per day to the test area (in each case one and always the same area on the inside of the forearm) in circular rubbing movements. The test time was 3 days. In each case suitable and in each case the same amounts of creams A and B were used. The sensitivity was assessed immediately and 3 minutes afterwards using those fingers which were not involved in the rubbing in. The sensitivity was assessed in each case three times at each time point.

The sensory results in the case of these two creams A and B were as follows:

Stickiness:

The stickiness was evaluated directly after application (t=0) and 3 minutes after application (t=3 min).

The average values are given. The evaluation scale ranged from 0 to 5. Considerable stickiness was evaluated as 5. In the case of the absence of stickiness, a 0 was awarded.

|  | t = 0 | t = 3 min |
| --- | --- | --- |
| Cream A: | 2.8 | 2.8 |
| Cream B: | 2.0 | 1.9 |

(All of the values were between 1 and 4).

Whitening:

The whitening was assessed directly after application. Again, the average values are given. The evaluation scale ranged from 0 to 5. Considerable whitening was evaluated as 5. In the absence of whitening, a 0 was awarded.

Cream A: 2.8
Cream B: 1.9

(All of the values were between 1 and 4).

Ability to Absorb:

The ability to absorb was assessed directly after application (t=0) and 3 minutes after application (t =3 min). The average values are given. The evaluation scale ranged from 0 to 5. Slow absorption was evaluated as 5. Rapid absorption was evaluated as 0.

|  | t = 0 | t = 3 min |
| --- | --- | --- |
| Cream A: | 3.1 | 3.0 |
| Cream B: | 2.2 | 2.1 |

(All of the values were between 1 and 5).

Pleasant Feel on the Skin:

It was assessed how pleasant the feel on the skin was perceived 3 minutes after application. Again, the average values are given. The evaluation scale ranged from 0 to 5. An unpleasant feel on the skin was evaluated as 5. A pleasant feel on the skin was evaluated as 0.

Cream A: 2.5
Cream B: 1.8

(All of the values were between 1 and 4 in the case of cream A, and between 1 and 3 in the case of cream B).

Greasy Skin Feel:

It was assessed how greasy the feel on the skin was perceived 3 minutes after application. Again, the average values are given. The evaluation scale ranged from 0 to 5. A greasy feel on the skin was evaluated as 5. A nongreasy feel on the skin was evaluated as 0.

Cream A: 3.1
Cream B: 2.3

(All of the values were between 1 and 5 in the case of cream A, and between 1 and 4 in the case of cream B).

Feeling of Smoothness:

It was assessed how the smoothness of the skin was perceived 3 minutes after application. Again, the average values are given. The evaluation scale ranged from 0 to 5. A harsh feel on the skin was evaluated as 5. A smooth feel on the skin was evaluated as 0.

Cream A: 2.8
Cream B: 2.1

(All of the values were between 1 and 5).

In summary, the following picture emerged with regard to the sensory properties:

The subjects established a clear difference between the two cream formulations.

Cream B with the glycerol ether/diol combination according to the invention left behind a clearly detectable pleasant feel on the skin following application, which was described with the adjectives velvety
smooth
supple.

As regards the feel on the skin following application of the comparison formulation A without the glycerol ether, the following statements were made:

dry
rough
harsh.

It was particularly advantageously additionally established that the skin following application of the cream containing glycerol ether felt neither greasy nor sticky.

For comparison, composition C, which comprised only the glycerol ether but no glycerol, and composition D, which comprised neither glycerol ether (3% by weight of glycerol ether replaced by water) nor glycerol, were also investigated.

|  | % by wt. |
| --- | --- |
| Arachidyl alcohol/behenyl alcohol/arachidyl glucoside (standard commercial mixture Montanov ® 202) | 5 |
| Cetearyl octanoate (Lanol ® 1688) | 20 |
| Cetylstearyl alcohol | 1 |
| 1-(2-Ethylhexyl) glycerol ether (Sensiva ® SC 50) | 3 (or 0) |
| Polyacrylate-13/polyisobutene/polysorbate 20 (standard commercial mixture Sepiplus ® 400) | 0.2 |

|  | % by wt. |
|---|---|
| Water (completely demineralized) | 70.7 (or 73.7) |
| Benzyl alcohol/methylchloroisothiazolinone/methyl-isothiazolinone (standard commercial mixture Euxyl ® K 100) | 0.1 |
|  | 100 |

The result of the assessment was that the achieved effects do not measure up to the skincare effects achieved above for the combination of the glycerol ether/glycerol neither in the case of composition D nor in the case of composition C (with a content of 3.0% by weight of glycerol ether).

Example 2

Microbicidal Effect

Besides the sensory evaluation, the microbicidal effect of a composition according to the invention was also investigated.

A quantitative suspension experiment was carried out in accordance with DGHM against Microbacterium terrae.

Inactivator: Phosphate buffer+THS-NT

Starting germ count: $3.4 \times 10^9$

In each case, the Rf values are given.

The following compositions E, F and G were tested, the data being given in % by weight:

| Composition: | E | F | G |
|---|---|---|---|
| 1-(2-Ethylhexyl) glycerol ether | 0.1 |  | 0.1 |
| 1,2-Hexanediol/1,2-octanediol (1:1) | 0.6 | 0.6 | 0.6 |
| Water (completely demineralized) | 99.3 | 99.4 | 99.9 |

Compositions F and G do not belong to the invention and serve for comparison purposes.

The resulting Rf values are given in the table below.

|  | Contact time | | |
|---|---|---|---|
|  | 15 min | 30 min | 60 min |
| E | 0 | 1.76 | 3.07 |
| F | 0 | 0 | 0 |
| G | 0 | 0 | 0 |

Result:

The combination of glycerol ether with a diol mixture (E) has a better effect, at a comparable concentration, than the diol mixture (F) on its own and the glycerol ether (G) on its own. This gives rise to a considerable increase in the effect for a diol mixture (F) as a result of the addition of glycerol ether (G) which, on account of the lack of an effect of the glycerol ether on its own, could not be expected. Synergism is present.

Example 3

Microbicidal Effect

A composition was tested which comprised 30% by weight of 1-(2-ethylhexyl) glycerol ether and 70% by weight of 1,2-octanediol.

It exhibits good results with regard to skin moisture, deodorizing effect and increase in the preservative effect of other preservatives, such as, for example, of parabens, in particular methyl paraben, or phenoxyethanol e.g. towards *Aspergillus niger, Candida albicans, Staphylococcus aureus, Pseudomonas aeruginose* and *Eschirichia coli*.

The invention claimed is:

1. A composition comprising:
   10% to 40% by weight of 1-(2-ethylhexyl) glycerol ether; and
   1,2-octanediol,
   wherein the composition is not an aftershave formulation which comprises 1-(2-ethylhexyl) glycerol ether, glycerol, and ethanol, and the composition is not a day cream which comprises 1-dodecyl glycerol ether and glycerol.

2. The composition according to claim 1, wherein the composition consists of 15% to 35% by weight of 1-(2-ethylhexyl) glycerol ether and 1,2-octanediol.

3. The composition according to claim 1, further comprising complexing agents and/or solubility promoters.

* * * * *